United States Patent
Winningham

(10) Patent No.: US 11,317,661 B2
(45) Date of Patent: May 3, 2022

(54) ARM WARMING DEVICE

(71) Applicant: Matthew Winningham, Royal Oak, MI (US)

(72) Inventor: Matthew Winningham, Royal Oak, MI (US)

(73) Assignee: Matthew Winningham, Royal Oak, MI (US)

( * ) Notice: Subject to any disclaimer, the term of this patent is extended or adjusted under 35 U.S.C. 154(b) by 45 days.

(21) Appl. No.: 16/239,842

(22) Filed: Jan. 4, 2019

(65) Prior Publication Data

US 2020/0214369 A1 Jul. 9, 2020

(51) Int. Cl.
*A41D 13/005* (2006.01)
*A41D 13/08* (2006.01)
*A61F 7/02* (2006.01)

(52) U.S. Cl.
CPC ......... *A41D 13/0058* (2013.01); *A41D 13/08* (2013.01); *A41D 13/0051* (2013.01); *A41D 2400/10* (2013.01); *A61F 2007/023* (2013.01)

(58) Field of Classification Search
CPC ................ A41D 13/0058; A41D 13/08; A41D 13/0051; A41D 2400/10; A41D 27/20; A61F 2007/023; A61F 2007/0029; A61F 7/007; A61F 7/003; A61F 7/0031; A61F 7/0032; A61F 7/0034; A61F 7/0071; A61F 7/0078; A61F 7/0086; A61F 7/0088; A61F 7/0093; A61F 7/0225; A61F 7/0228; A61F 7/0257
USPC ......................................................... 219/211
See application file for complete search history.

(56) References Cited

U.S. PATENT DOCUMENTS

| | | | | |
|---|---|---|---|---|
| 807,628 | A * | 12/1905 | Mark ..................... | A41D 13/08 2/59 |
| 1,117,077 | A * | 11/1914 | Mooney ................. | A41D 13/08 2/16 |
| 1,141,656 | A * | 6/1915 | Rosenbaum et al. .. | A41D 13/08 2/59 |
| 1,285,917 | A * | 11/1918 | Bradley et al. ......... | A41D 1/04 2/91 |
| 1,346,092 | A * | 7/1920 | Hullinger ................. | A61F 2/58 623/58 |
| 1,561,400 | A * | 11/1925 | Begg ........................ | A61F 5/50 128/881 |
| 1,796,782 | A * | 3/1931 | Gasperini ............... | A41D 13/08 2/87 |
| 2,150,069 | A * | 3/1939 | Koleno ................... | A41D 13/08 2/59 |

(Continued)

OTHER PUBLICATIONS

Rag Arm, http://www.rag-arm.com/ (last visited Jan. 4, 2019).

(Continued)

*Primary Examiner* — Jocelyn Bravo
(74) *Attorney, Agent, or Firm* — Dickinson Wright PLLC

(57) ABSTRACT

An arm warming device including a sleeve. A shoulder cover is connected to a proximal end of the sleeve. A strap is connected to the shoulder cover to secure the arm warming device to the user. A heating element is disposed within the sleeve for applying heat to the arm of the user. The heating element comprises far infrared fiber material. The sleeve includes an interior layer, a central layer, and an outer layer of a substantially waterproof material. The heating element is integrated with the central layer for applying heat to the arm of the user.

4 Claims, 5 Drawing Sheets

(56) References Cited

U.S. PATENT DOCUMENTS

| | | | | |
|---|---|---|---|---|
| 3,748,436 A * | 7/1973 | Cossaboom | H05B 3/342 | 219/211 |
| 4,006,495 A * | 2/1977 | Jones | A41D 3/00 | 2/93 |
| 4,089,032 A * | 5/1978 | Dell Orfano | H01C 7/12 | 361/111 |
| 4,229,833 A * | 10/1980 | Cox | A41D 13/08 | 2/16 |
| 4,356,570 A * | 11/1982 | Vernon | A41D 13/08 | 2/126 |
| 4,569,087 A * | 2/1986 | Kerwin | A41D 13/0053 | 2/126 |
| 4,851,805 A * | 7/1989 | Poerschke | H01H 69/02 | 337/231 |
| 4,985,934 A * | 1/1991 | Perry | A41D 13/08 | 2/125 |
| 5,023,430 A * | 6/1991 | Brekkestran | A41D 13/0051 | 2/69 |
| 5,032,705 A * | 7/1991 | Batcheller | A41D 13/0051 | 219/211 |
| 5,201,075 A * | 4/1993 | Svetich | A41D 15/00 | 2/108 |
| 5,357,633 A * | 10/1994 | Rael | A41D 13/08 | 2/126 |
| 5,528,673 A * | 6/1996 | Rosenthal | H04M 1/82 | 379/102.03 |
| 5,563,472 A * | 10/1996 | Cassidy | H05B 47/21 | 315/119 |
| 5,636,380 A * | 6/1997 | Schindler | A41D 13/005 | 2/69 |
| 5,638,546 A * | 6/1997 | Vita | A41D 13/08 | 2/16 |
| 5,667,447 A * | 9/1997 | Perham | A63B 69/0059 | 473/212 |
| 5,909,801 A * | 6/1999 | Coffman | A41D 19/0041 | 2/159 |
| 5,974,586 A * | 11/1999 | Reinoso | A41D 13/08 | 2/310 |
| 6,052,824 A * | 4/2000 | May | A41D 13/08 | 2/16 |
| 6,223,565 B1 * | 5/2001 | Cooper | A41D 13/08 | 66/172 E |
| 6,229,123 B1 * | 5/2001 | Kochman | A41D 13/0051 | 219/529 |
| 6,268,595 B1 * | 7/2001 | Haenel | A61F 7/02 | 219/211 |
| 8,133,264 B1 * | 3/2012 | LaFontaine | A61F 7/007 | 2/125 |
| 8,602,073 B2 * | 12/2013 | Swain | A45F 3/00 | 150/106 |
| 8,667,613 B2 * | 3/2014 | Blakely | A41D 13/08 | 2/16 |
| 9,027,164 B2 * | 5/2015 | Seiler | A41D 1/22 | 2/16 |
| 9,295,291 B2 * | 3/2016 | Blakely | A41D 13/08 | |
| 9,427,033 B2 * | 8/2016 | Blakely | A41D 13/08 | |
| 9,955,742 B2 * | 5/2018 | Lopez | A41D 31/00 | |
| 10,470,509 B1 * | 11/2019 | Knott | A41D 13/002 | |
| 10,550,501 B2 * | 2/2020 | Achtymichuk | A41D 31/14 | |
| 10,638,801 B2 * | 5/2020 | Verma | A41F 19/00 | |
| 2001/0032347 A1 * | 10/2001 | Redwood | A61B 5/6806 | 2/160 |
| 2001/0047992 A1 * | 12/2001 | Deangelis | A41D 13/0051 | 219/529 |
| 2003/0013948 A1 * | 1/2003 | Russell | A61B 5/04282 | 600/372 |
| 2004/0163154 A1 * | 8/2004 | Cooper | A41D 13/08 | 2/69 |
| 2004/0225049 A1 * | 11/2004 | Komuro | D01F 1/09 | 524/403 |
| 2005/0167412 A1 * | 8/2005 | Anson | A41D 13/0051 | 219/211 |
| 2006/0001727 A1 * | 1/2006 | Haas | B41J 2/375 | 347/194 |
| 2006/0179546 A1 * | 8/2006 | Ko | A41B 11/12 | 2/239 |
| 2007/0048595 A1 * | 3/2007 | Graham | H01M 2/26 | 429/62 |
| 2007/0278201 A1 * | 12/2007 | Jones | A43B 7/025 | 219/211 |
| 2007/0283481 A1 * | 12/2007 | Rawlings | A41D 7/008 | 2/114 |
| 2008/0023460 A1 * | 1/2008 | Huang | H05B 3/342 | 219/211 |
| 2008/0116189 A1 * | 5/2008 | Fernandez | A41D 13/0051 | 219/211 |
| 2009/0000002 A1 * | 1/2009 | Hadash | A41D 13/0058 | 2/16 |
| 2009/0019614 A1 * | 1/2009 | Hagihara | A41D 19/01529 | 2/16 |
| 2010/0138977 A1 * | 6/2010 | Lin | B29C 66/431 | 2/125 |
| 2010/0253501 A1 * | 10/2010 | Gibson | H05B 47/155 | 340/475 |
| 2011/0108538 A1 * | 5/2011 | Gray | H05B 1/0272 | 219/211 |
| 2011/0167529 A1 * | 7/2011 | Anderson | A41D 13/08 | 2/2.5 |
| 2011/0219509 A1 * | 9/2011 | Kern | A63B 69/0059 | 2/16 |
| 2011/0296591 A1 * | 12/2011 | Park | A41B 9/00 | 2/401 |
| 2011/0314585 A1 * | 12/2011 | Blakely | A41D 13/08 | 2/69 |
| 2012/0210488 A1 * | 8/2012 | Blakely | A41D 19/01 | 2/69 |
| 2013/0037531 A1 * | 2/2013 | Gray | H05B 1/0272 | 219/211 |
| 2014/0150321 A1 * | 6/2014 | Fitzgerald | A41D 13/0002 | 42/90 |
| 2014/0246416 A1 * | 9/2014 | White | A41D 13/01 | 219/211 |
| 2014/0356574 A1 * | 12/2014 | Conolly | B32B 5/02 | 428/138 |
| 2015/0000003 A1 * | 1/2015 | Blakely | A41D 13/08 | 2/69 |
| 2015/0060430 A1 * | 3/2015 | Tsuge | H05B 3/00 | 219/211 |
| 2015/0083705 A1 * | 3/2015 | Cronn | H05B 3/347 | 219/211 |
| 2016/0058089 A1 * | 3/2016 | Niedrich | A42B 1/22 | 2/172 |
| 2016/0091225 A1 * | 3/2016 | Camacho Perez | C23C 22/73 | 428/34.1 |
| 2016/0128393 A1 * | 5/2016 | Janda | A41D 13/0051 | 219/211 |
| 2016/0331054 A1 * | 11/2016 | Coza | A41D 31/145 | |
| 2016/0374411 A1 * | 12/2016 | Brooks | A61F 7/007 | 165/104.21 |
| 2017/0332442 A1 * | 11/2017 | Strecker | A41D 13/0051 | |
| 2018/0103694 A1 * | 4/2018 | Fortenbacher | H05B 1/0272 | |
| 2018/0289082 A1 * | 10/2018 | Burrows | A41D 13/0051 | |
| 2018/0317573 A1 * | 11/2018 | Devito | A41D 13/0051 | |
| 2019/0008677 A1 * | 1/2019 | Burge | A61F 7/08 | |
| 2019/0216147 A1 * | 7/2019 | Lamontia | B32B 27/40 | |

OTHER PUBLICATIONS

Innovated Sports, the Heater Sleeve, http://www.isheat.com/the-heater-sleeve.html (last visited Jan. 4, 2019).

* cited by examiner

ARM WARMING DEVICE

TECHNICAL FIELD

The present disclosure relates generally to a limb protection garment for use by an individual seeking therapeutic relief. More particularly, the present disclosure relates to an improved arm warming device for use during athletic competition.

BACKGROUND OF THE DISCLOSURE

In conventional athletic practice, an athlete will generally desire to stay warm and maintain a certain degree of readiness during a game when the athlete is resting. A prime example of this is a baseball pitcher who generally desires to maintain a degree of readiness between innings. Specifically, the pitcher will generally insert their throwing arm into a sleeve of a jacket to retain warmth and prevent their arm from becoming cold while sitting in the dugout. However, such jackets are not ideal and may present various problems, such as, but not limited to, failing to the keep the pitchers arm at the appropriate temperature to maintain readiness and being unduly burdensome and inefficient as full size jackets can be bulky.

Additionally, a full size jacket is not conducive to quick removal when the pitcher must return to the mound. As such, and to maintain full readiness, the full jacket is generally not used so that the pitcher can quickly remove their still warm arm from the sleeve and return to the mound. This may present a hazard caused by a loose clothing garment in a dugout full of athletes going out to the field of play and returning from the field of play. The jacket is bulky and may catch on other players, equipment, or other gear in the dugout, which may cause injury or embarrassment.

SUMMARY OF THE INVENTION

It is therefore an aspect of the present disclosure to provide an arm warming device that will overcome the shortcomings of the prior art as described above.

It is another aspect of the present disclosure to provide an arm warming device that will give thermal protection to an arm and shoulder of a user, so as to maintain and/or therapeutically alter a user's body heat when the user is idle.

It is another aspect of the present disclosure to provide an arm warming device that can quickly and releasably be secured onto the arm of a user.

It is another aspect of the present disclosure to provide an arm warming device that can reliably be heated for long periods of time.

It is another aspect of the present disclosure to provide an arm warming device that can provide localized heating to specific regions of the arm of a user.

In accordance with the above and the other aspects of the present disclosure, an arm warming device is provided. The arm warming device includes a sleeve extending between a proximal end and a distal end for receiving an arm of a user. A shoulder cover is connected to the proximal end of the sleeve for covering a shoulder of the user. A strap is connected to the shoulder cover for being wrapped about a torso of the user to secure the arm warming device to the user. A heating element is disposed within the sleeve for applying heat to the arm of the user. The heating element comprises far infrared fiber material.

A further arm warming device is provided including a sleeve extending between a proximal end and a distal end for receiving an arm of a user. A shoulder cover is connected to the proximal end of the sleeve for covering a shoulder of the user. A strap is connected to the shoulder cover for being wrapped about a torso of the user to secure the athletic device to the user. The sleeve includes an interior layer for engaging the arm of the user, a central layer, and an outer layer of a substantially waterproof material. A heating element comprising far infrared fiber material is integrated with the central layer for applying heat to the arm of the user.

BRIEF DESCRIPTION OF THE DRAWINGS

The drawings described herein are provided to illustrate selected, non-limiting embodiments without limiting the intended scope of protection afforded to the present disclosure.

FIG. 1A is a front view of a connector of a connection terminal of a battery pack of the arm warming device of FIG. 1;

DETAILED DESCRIPTION OF THE ENABLING EMBODIMENTS

In the following description, details are set forth to provide an understanding of the present disclosure. In some instances, certain systems, structures, and techniques have not been described or shown in detail in order not to obscure the disclosure.

Figure 3:
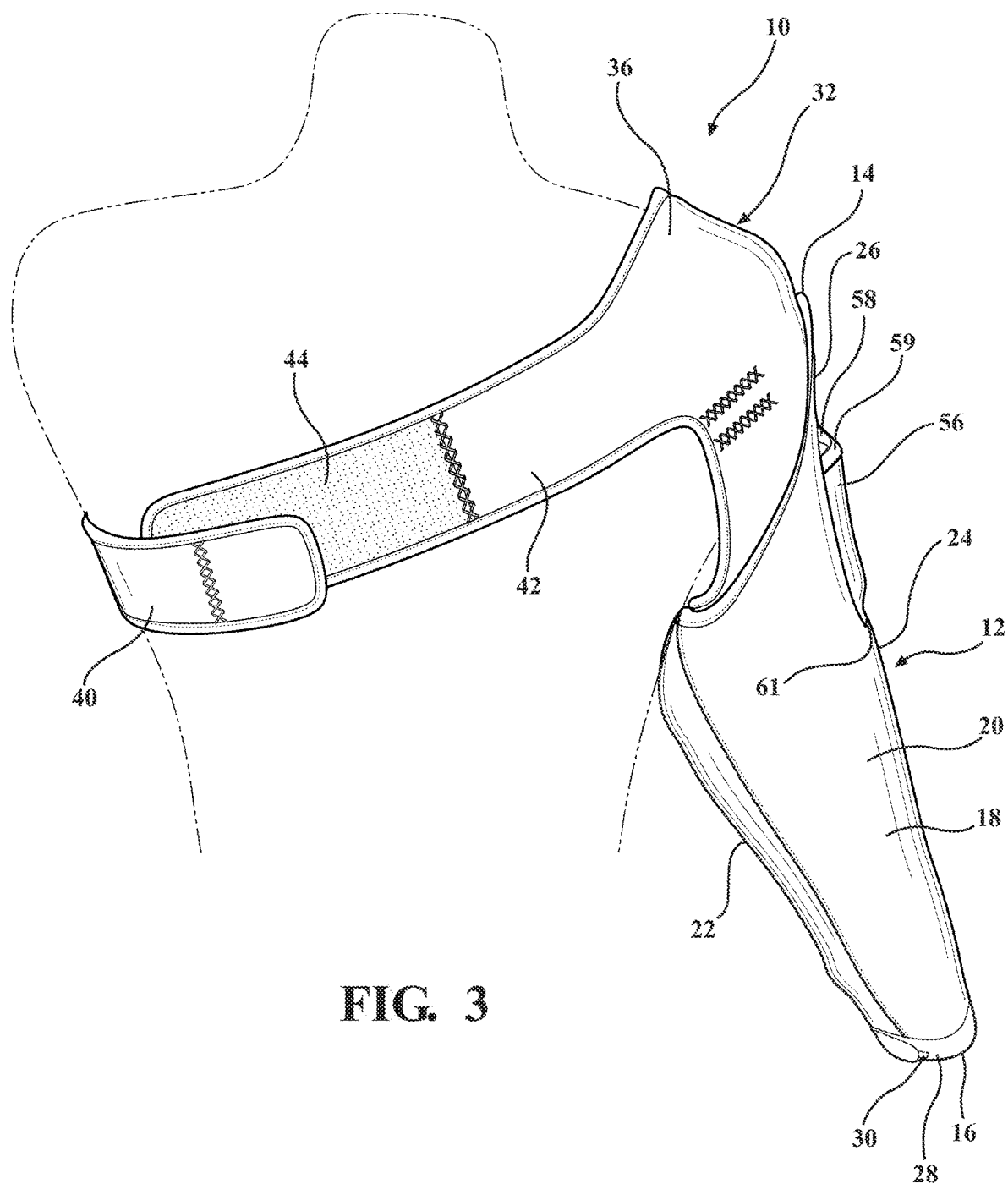
FIG. 3 is a back view of the arm warming device of FIG. 1.
Figure 4:
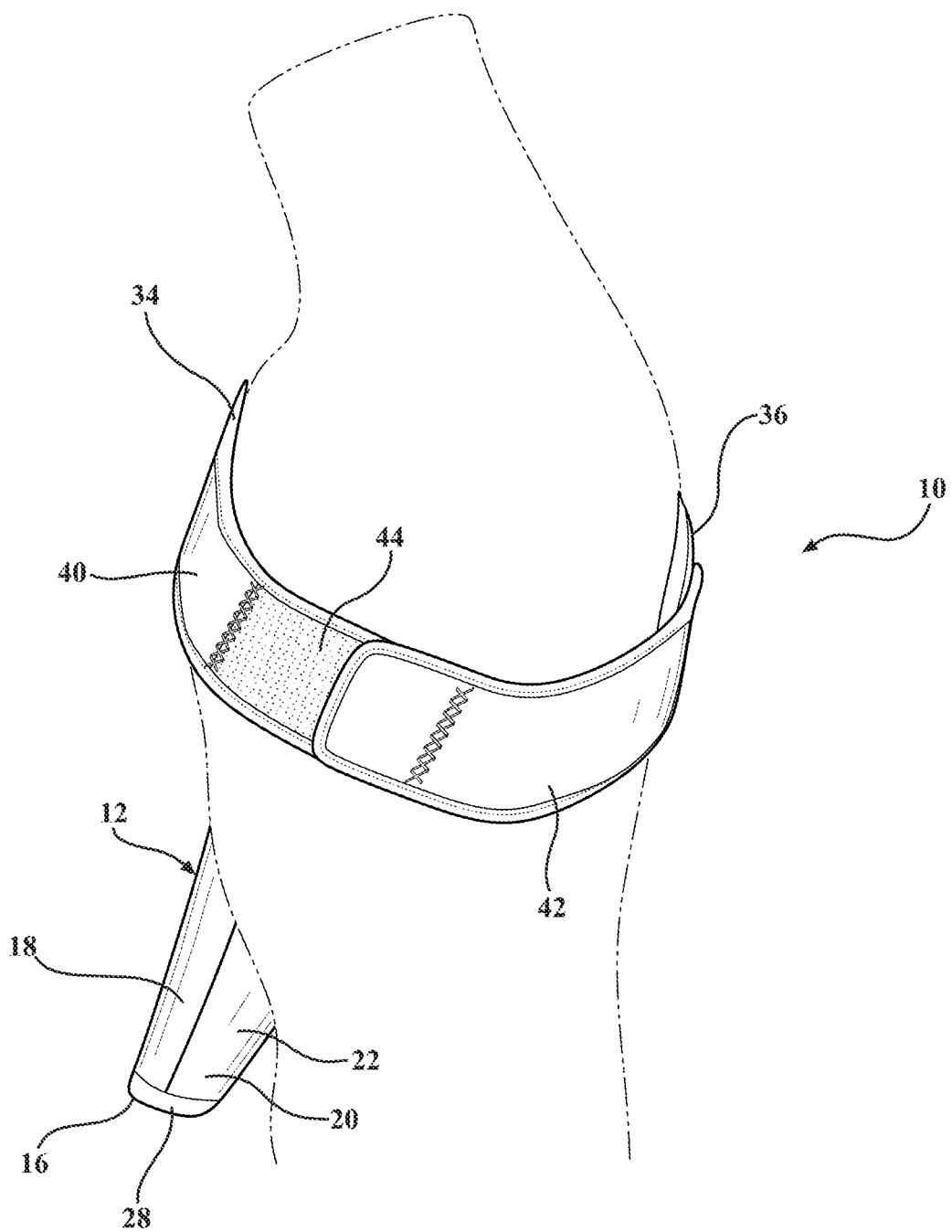
FIG. 4 is a right side perspective view of the arm warming device of FIG. 1.
Figure 5:
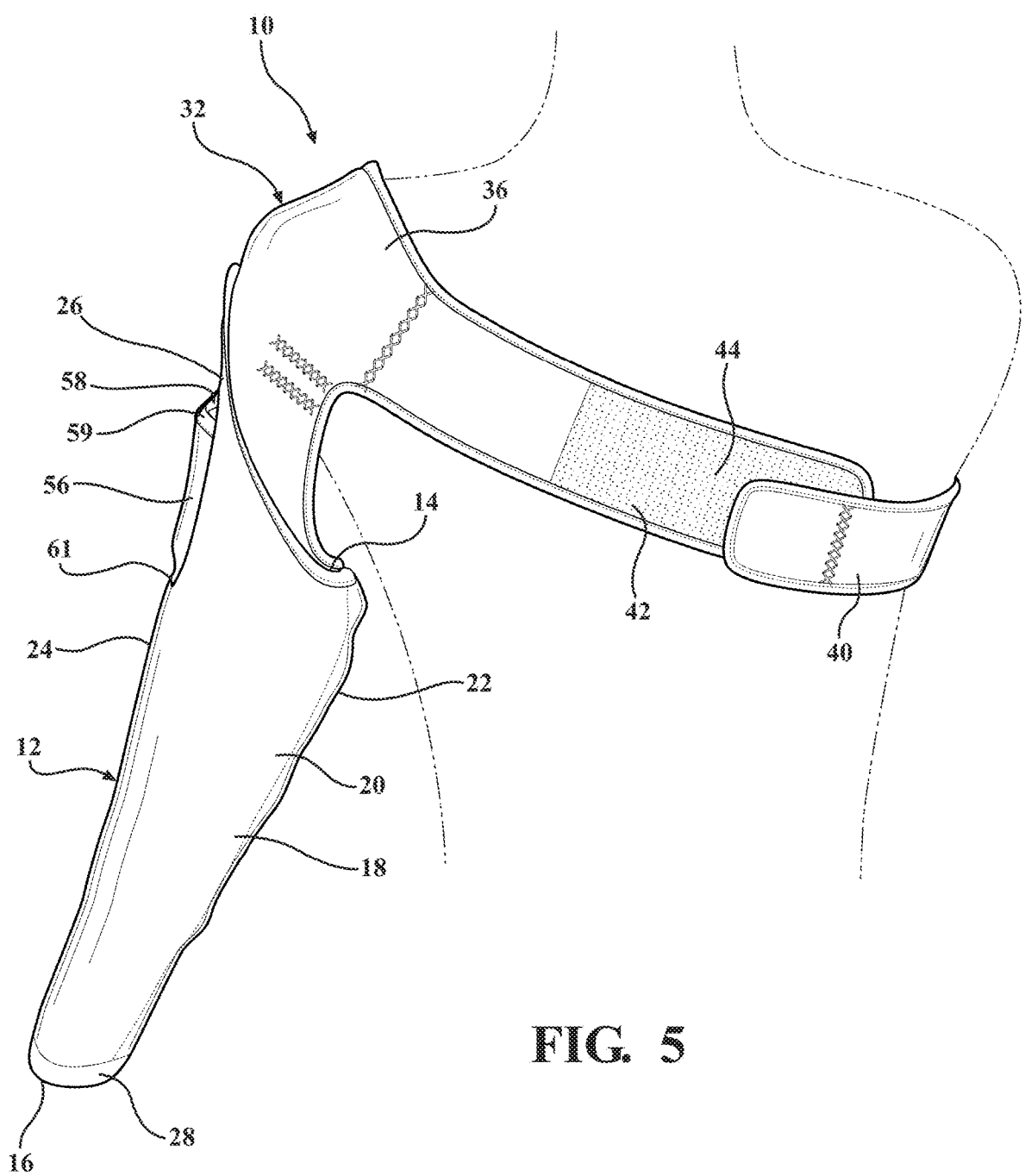
FIG. 5 is a back view of an alternate embodiment of an arm warming device which is configured to be positioned on a left arm of a user.

Referring to the figures, wherein like numerals indicate corresponding parts throughout the several views, a warning device 10 is generally shown. The warming device 10 includes a sleeve 12 of generally or substantially tubular shape that extends between a proximal end 14 and a distal end 16 along a midsection 18 for receiving an arm of a user. It should be understood that the sleeve 12 may be adapted to insertably receive only a portion or all of the user's arm. The sleeve 12 could alternatively be configured to receive a leg of the user. The sleeve 12 may also be worn on either the left or right arm of the user (see e.g., FIGS. 3 and 5). The sleeve 12 has an outer surface 20 that has an inner region 22 for facing the torso of the user and an outer region 24 opposite the inner region 22 for facing away from the torso of the user. The outer region 24 extends past the inner region 22 at the proximal end 14 along a flap portion 26.

A wrist band 28 is positioned at the distal end 16 of the sleeve 12 for allowing a user to tighten the distal end 16 of the sleeve 12 about the user's wrist. The wrist band 28 includes a securing device 30 such as an arrangement of hook and loop fasteners for allowing the user to secure the wrist band 28 in a desired position.

A protective, flexible shoulder cover 32 is connected to the flap portion 26 for covering and/or protecting a shoulder of the user and for assisting the sleeve 12 in retaining the shape of the sleeve 12 and its position on the arm of the user.

The shoulder cover 32 has a front region 34 for extending toward a chest of the user and a back region 36 for extending toward a back of the user.

A strap 40, 42 is connected to the shoulder cover 32 for extending around the body of the user and returning to the shoulder cover 32. The strap 40, 42 is adapted to secure the sleeve 12 to the arm of the user and to assist in storing or hanging the sleeve 12 when not in use. The strap 40, 42 includes a first strap portion 40 that extends from the front region 34 of the shoulder cover 32 for overlying the chest of the user and a second strap portion 42 that extends from the back region 36 of the shoulder cover 32 for overlying the back of the user. A fastening device 44, such as a hook and loop arrangement, detachably connects the first and second strap portions 40, 42. It should be appreciated that the shoulder cover 32 and strap 40, 42 are sized and arranged such that the sleeve 12 may be worn on either the left or right arm of the user.

It should be appreciated that the aforementioned arrangement of the sleeve 12, shoulder cover 32, and strap 40, 42 allows the warming device 10 to easily and quickly be put on and removed by a user.

The sleeve 12 has an inside layer 46 for engaging the arm of the user, the inside layer 46 is of a first material such as a cotton or fleece. The sleeve 12 further has a central layer 48 that has a heating element 49 integrated therein. The heating element 49 may comprise strands of far infrared fiber material ("FIR material"). For example, the heating element 49 may comprise a plurality (e.g., thousands or millions) of strands of carbon fiber, a plurality (e.g., thousands or millions) of strains of ceramic fiber, a plurality of strands of other suitable FIR material, or a combination thereof. FIR material may allow the heating element 49 to heat in a relatively short period (e.g., 3 seconds) and may be compactable, such that, the sleeve 12 may be compacted and stored or carried. Additionally, or alternatively, the FIR material may allow the heating element 49 to be water resistant. The strands of FIR material of the heating element 49 may be stitched together and may be integrated with fibers, strands, or other suitable material of the central layer 48. The central layer 48 may comprise a suitable fabric or fiber material, such as cotton, fleece, carbon fiber, or other suitable fabric or fiber material. The stitched together strands of FIR material may form connections or ends which may connect the heating element 49 to a connector, as will be described. The strands of FIR material of the heating element 49 are configured to receive energy and to provide far infrared radiation (e.g., electromagnetic radiation having a wavelength between substantially 15 micrometers and substantially 1 millimeter) to a portion of the user using the received energy. The sleeve 12 further has an outer shell layer 50 of a water resistant or substantially water proof material such as a nylon.

The heating element 49 of the central layer 48 is configured to provide heat to the user's muscles, joints, ligaments, or tendons to improve the therapeutic effect. For example, the strands of FIR material generate heat at a portion of the heating element 49 that makes contact with a portion of the user via the sleeve 12. Conversely, FIR material does not generate heat at portions of the heating element 49 not making contact with the user. The heat may then be transferred to muscles, joints, ligaments, or tendons of the user proximate the portion of the user that makes contact with the strands of FIR material via the sleeve 12.

A flap 56 is connected to the outer region of the sleeve 12 to define a pocket 58. The pocket 58 may have an open end 59 and a closed end 61. A closing device 60 such as one or more buttons, a zipper or hook and loop arrangement allows the open end 59 of the pocket 58 to be selectively be opened and closed.

An end of the heating element 49 presents a connection plug 62 that extends into the pocket 58 from inside the sleeve 12. For example, the stitched together strands of the FIR material of the heating element 49 may be electrically connected to the connection plug 62. According to the example embodiment, the connection plug 62 is a USB connector but other styles of connection plugs may be utilized. A battery pack 64 is removeably positioned inside the pocket 62. The battery pack 64 has a connection terminal 66 (shown in FIG. 1A) for detachably being connected to the connection plug 62. According to the example embodiment, the connection terminal 66 is a USB terminal that is configured to receive the USB connector style connection plug 62, but other style of connection terminals may be used.

A rechargeable battery 68 positioned is in the battery pack 64. According to the example embodiment, the rechargeable battery 68 is a lithium ion battery, however other sources capable of supplying energy to the heating element 49 may be utilized. A power cable 70 may detachably connected to the connection terminal 66 for charging the rechargeable battery 68. It should be appreciated that the removable arrangement of the battery pack 64 allows the battery pack to easily be charged separate from the sleeve 12. Furthermore the battery pack is small in size and discrete, thus allowing it to be comfortably concealed within the pocket 62. It should also be appreciated that different batteries 68 may be swapped in and out of the battery pack 64 to allow continuous use of the warming device while batteries are being charged 68.

Figure 1:
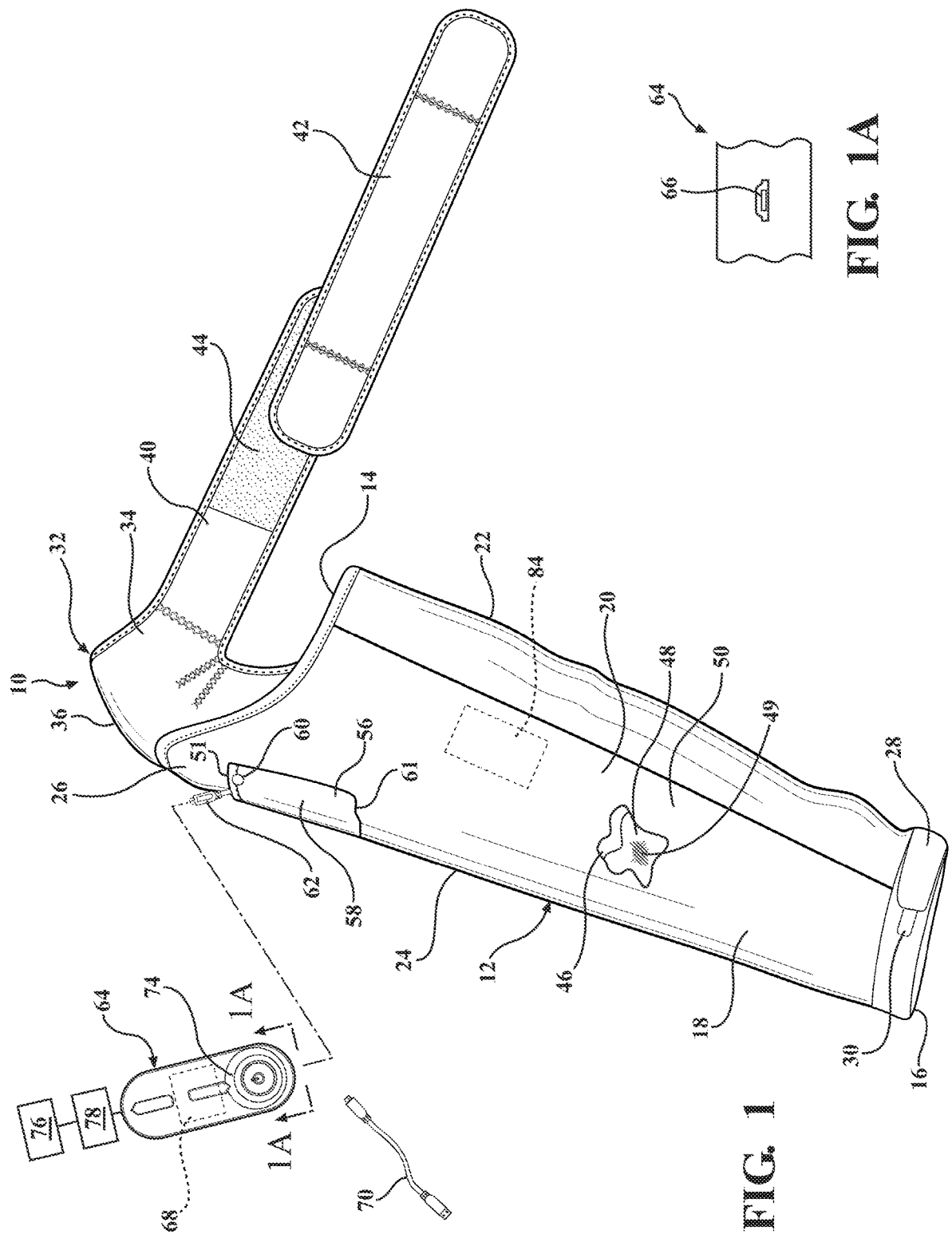
FIG. 1 is a front perspective, exploded view of an example embodiment of an arm warming device in accordance with an aspect of the subject disclosure.
Figure 2:
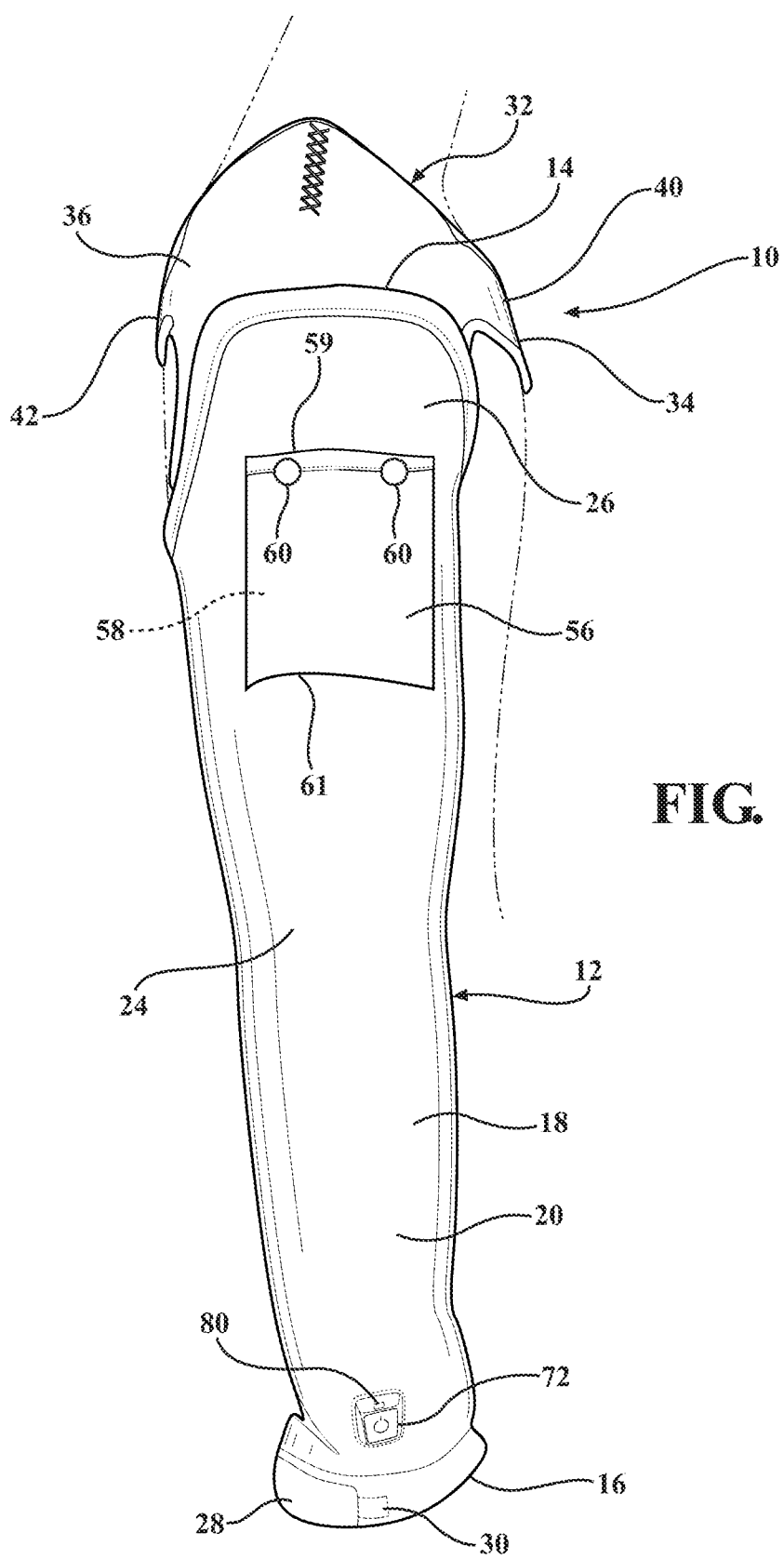
FIG. 2 is a left side perspective view of the arm warming device of FIG. 1.

As best shown in FIGS. 1 and 2, first and second power buttons 72, 74 (and optionally, a third power button, (not shown)) are disposed on a portion of the sleeve 12 and electrically connected to heating element 49. For example, as will be described, the first power button 72, the second power button 74, and optionally the third power button may be selectively actuated the temperature setting of the heating element 49 between a high setting, a medium setting, and a low setting. Furthermore, as schematically illustrated in FIG. 1, a controller 76 is electrically connected to the first and second power buttons 72, 74 and the heating element 49 to selectively activate heating properties of the FIR material of the heating element 49 at one of a plurality of predetermined temperature modes. The controller 76 may be contained within the battery pack 64 or may coupled to the sleeve 12 at other locations. The temperature modes may include a first temperature mode which heats the heating element 49 to a first temperature, a second temperature mode which heats the heating element 49 to a second temperature, a third temperature mode which heats the heating element 49 to a third temperature and off mode in which the heating element 49 is not activated. The controller 76 may be configured such that the temperature modes and the off mode are cycled in response to pressing the first or second power buttons 72, 74. A pico fuse 78 is electrically connected to the controller 76 and the heating element 49 for deactivating the heating element 49 if the heating element 49 incidentally exceeds a predetermined temperature or if an electrical component fails causing the pico fuse 78 to deactivate the heating element 49. Additionally, or alternatively, the heating element 49 after a predetermined period, such as, 10 minutes. For example, the first power button 72 and/or the second power button 47 may be configured to deactivate the heating element 49 automatically after the predetermined period to conserver battery life and prevent overheating.

As best shown in FIG. 2, the first power button 72 is attached to the sleeve 12 adjacent to the distal end 16. A first light source 80 is positioned inside the first power button 72 and is configured to illuminate the first power button 72 at a predetermined color based on what temperature mode is activated. The first light source 80 may also be configured to illuminate the first power button 72 at other colors to display to the user other pieces of information such as the amount of power remaining in the battery 68 or the amount of uninterrupted time remaining in the battery 68. It should be appreciated that any number of first light sources 80 may be used to simultaneously provide various pieces of information to the user.

As best shown in FIG. 1, the second power button 74 is positioned on the battery pack 64. A second light source 82 is positioned inside the second power button 74 and is configured to illuminate the second power button 74 at a predetermined color based on what temperature mode is activated. Like the first light source 80, the second light source 82 may also be configured to illuminate the second power button 74 at other colors to display to the user other pieces of information such as the amount of power remaining in the battery 68 or the amount of uninterrupted time remaining in the battery 68. It should be appreciated that any number of second light sources 80 may be used to simultaneously provide various pieces of information to the user.

According to a further aspect of the disclosure, in addition to the heating element 49, other heating elements 84 may be utilized separately, or in conjunction with the heating element 49. Such elements 84 may include a far infrared ("FIR") carbon heating pad, or any other heating pad, capable of producing a sustainable heating effect for a period of time. The elements 84 may be positioned inside the pocket 58. Any number of pockets 58 may be utilized and the pockets 58 may be positioned at other locations along the sleeve 12 to provide localized heating at targeted locations.

The foregoing disclosure has been described in accordance with the relevant legal standards, thus the description is exemplary rather than limiting in nature. Variations and modifications to the disclosed embodiment may become apparent to those skilled in the art and do come within the scope of the disclosure. Such variations are not to be regarded as a departure from the disclosure, and all such modifications are intended to be included within the scope of the disclosure. Those skilled in the art will recognize that concepts disclosed in association with an example enclosure assembly can likewise be implemented into many other systems to control one or more operations and/or functions. Accordingly, the scope of legal protection afforded this disclosure can only be determined by studying the following claims.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer, or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated degrees or at other orientations) and the spatially relative descriptions used herein interpreted accordingly.

What is claimed is:

1. An electrically heated single sleeve device for warming a single arm of a user, comprising:
   a sleeve extending between a proximal end and a distal end for receiving the arm of the user;
   the sleeve including an interior layer for engaging the arm of the user, a central layer comprising a heating element comprised of a far infrared material, and an outer layer of a water resistant material;
   a shoulder cover connected to the proximal end of the sleeve for covering a shoulder of the user, the shoulder cover including a front region configured to cover a front portion of the user's shoulder, and a back region opposite the front region and configured to cover a rear portion of the user's shoulder;

a first strap extending from the front region of the shoulder cover and configured to overlie a chest of the user, a second strap extending from the back region of the shoulder cover and configured to overlie a back of the user, and a hook and loop fastening device located adjacent to an end of each of the first and second straps and configured to detachably connect the first and second straps to one another to provide quick attachment and removal of the first and second straps to one another, and wherein the hook and loop fastening device of at least one of the first and second straps extends across substantially an entirety of a width of the strap;

the sleeve defining at least one pocket adjacent to the proximal end of the sleeve and adjacent to the shoulder cover;

a connection plug electrically connected to the heating element and received in the pocket;

a battery pack removeably positioned inside the pocket and detachably connected to the connection plug and including a battery for providing power to the heating element, and including a controller configured to activate a plurality of heating modes of the heating element;

a first power button positioned on the battery pack and configured to allow a user to select one of the plurality of heating modes;

a second power button disposed on the sleeve adjacent to the distal end and electrically connected to the controller for allowing the user to select one of the plurality of heating modes;

the controller further configured to deactivate the heating element after a predetermined period of time;

a first light source positioned inside the first power button and configured to illuminate the first power button to one of a plurality of different colors based on the selected one of the plurality of heating modes; and a second light source positioned inside the second power button and configured to illuminate the second power button to one of a plurality of different colors based on the selected one of the plurality of heating modes;

wherein the sleeve device does not include more than one sleeve.

2. The electrically heated single sleeve device for warming a single arm of a user as set forth in claim 1 wherein the far infrared fiber material of the heating element includes a plurality of carbon fiber strands.

3. The electrically heated single sleeve device for warming a single arm of a user as set forth in claim 1 wherein the battery is a rechargeable lithium ion battery.

4. The electrically heated single sleeve device for warming a single arm of a user as set forth in claim 1 wherein a fuse is electrically connected to the heating element for deactivating the heating element in response to the heating element exceeding a predetermined temperature.

* * * * *